(12) United States Patent
Heidemann et al.

(10) Patent No.: US 6,849,574 B1
(45) Date of Patent: Feb. 1, 2005

(54) SILVER- AND VANADIUM-CONTAINING MULTIMETAL OXIDE AND ITS USE

(75) Inventors: Thomas Heidemann, Weinheim (DE); Hartmut Hibst, Schriesheim (DE); Stefan Bauer, Ludwigshafen (DE); Ulf Dietrich, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,996
(22) PCT Filed: Nov. 10, 1999
(86) PCT No.: PCT/EP99/08579

§ 371 (c)(1),
(2), (4) Date: May 3, 2001

(87) PCT Pub. No.: WO00/27753

PCT Pub. Date: May 18, 2000

(30) Foreign Application Priority Data

Nov. 10, 1998 (DE) .................................. 198 51 786

(51) Int. Cl.$^7$ ...................... B01J 23/58; B01J 23/48; H01M 4/54; C01G 7/00
(52) U.S. Cl. .................. 502/330; 502/347; 429/219; 429/231.5; 549/248; 549/239; 423/604
(58) Field of Search ................ 429/219, 231.5; 423/604; 502/347, 330; 549/248, 239

(56) References Cited

U.S. PATENT DOCUMENTS

| | | | |
|---|---|---|---|
| 3,394,468 A | 7/1968 | Zeller | 34/583 |
| 3,485,876 A | 12/1969 | van de Mond | 568/430 |
| 3,684,741 A | 8/1972 | Friedrichsen | 502/209 |
| 3,799,886 A | 3/1974 | Felice | 502/350 |
| 3,871,445 A | 3/1975 | Wanka | 165/104.14 |
| 4,077,984 A | 3/1978 | Blechschmitt | 549/248 |
| 4,137,259 A | 1/1979 | Van Geem | 562/415 |
| 4,203,906 A | 5/1980 | Takada | 549/248 |
| 4,284,571 A | 8/1981 | Sato et al. | 549/248 |
| 4,665,200 A | 5/1987 | Nakanishi | 549/239 |
| 4,965,151 A | * 10/1990 | Takada et al. | 429/191 |
| 5,677,261 A | 10/1997 | Tenten | 502/439 |
| 5,695,892 A | 12/1997 | Leising et al. | 429/219 |
| 5,792,719 A | 8/1998 | Eberle | 502/178 |

FOREIGN PATENT DOCUMENTS

| | | |
|---|---|---|
| DE | 1 294 951 | 1/1970 |
| DE | 1 280 756 | 4/1970 |
| DE | 1 769998 | 2/1972 |
| DE | 2 106796 | 8/1972 |
| DE | 2 201528 | 11/1972 |
| DE | 25 46 268 | 4/1977 |
| DE | 28 30 765 | 1/1980 |
| DE | 28 47 163 | 6/1980 |
| DE | 197 05326 | 8/1998 |
| DE | 198 23262 | 12/1999 |
| EP | 163 231 | 12/1985 |
| EP | 256 352 | 2/1988 |
| EP | 286 448 | 10/1988 |
| EP | 447 267 | 9/1991 |
| EP | 714 700 | 6/1996 |
| EP | 856 490 | 8/1996 |
| EP | 744 214 | 11/1996 |
| GB | 1164316 | 9/1969 |
| JP | 44-29045 | 11/1969 |
| JP | 46-42883 | 12/1971 |
| RU | 2088 567 | 8/1997 |
| WO | 98/37967 | 9/1998 |

OTHER PUBLICATIONS

Andreikov et al., Kinet Kental. 22,963(1981).
Andreikov et al., Kinet Kental. 22, 1207 (1981).
Appl.Cataly, 1990, 267–278, Jun et al.
Bull.Soc.Chim.France 2817,1967, Casalot et al.
Mat.Res.Bull.,vol. 24,No. 12,1989,1501–13,Znaidi et al.
K. Towae et al., Ullmann's Enc. vol. A20,1992,181.
Wells, Struc.Inor.Chem,5thEd.,1984,621–625.
Rao etal.,Trans.Metal Oxides, 1995, 176–179.
Gmelin Hanbuch, 61, 1974,274–277.
Andreikov etal.,Perroi,Chem.vol.17,No. 3,155–158, 1990.
J.Cat.,vol. 129, 1991, 426–437, Hui–Liang et al.
ZH.Neorg.Khim, vol. 33, No. 7, 1988, 1833–35.

* cited by examiner

Primary Examiner—Cecilia Tsang
Assistant Examiner—Taylor Victor Oh
(74) Attorney, Agent, or Firm—Keil & Weinkauf

(57) ABSTRACT

A multimetal oxide of the formula I $$Ag_{a-b}M_bV_2O_x \cdot c\, H_2O, \quad\quad I$$

Figure 1:
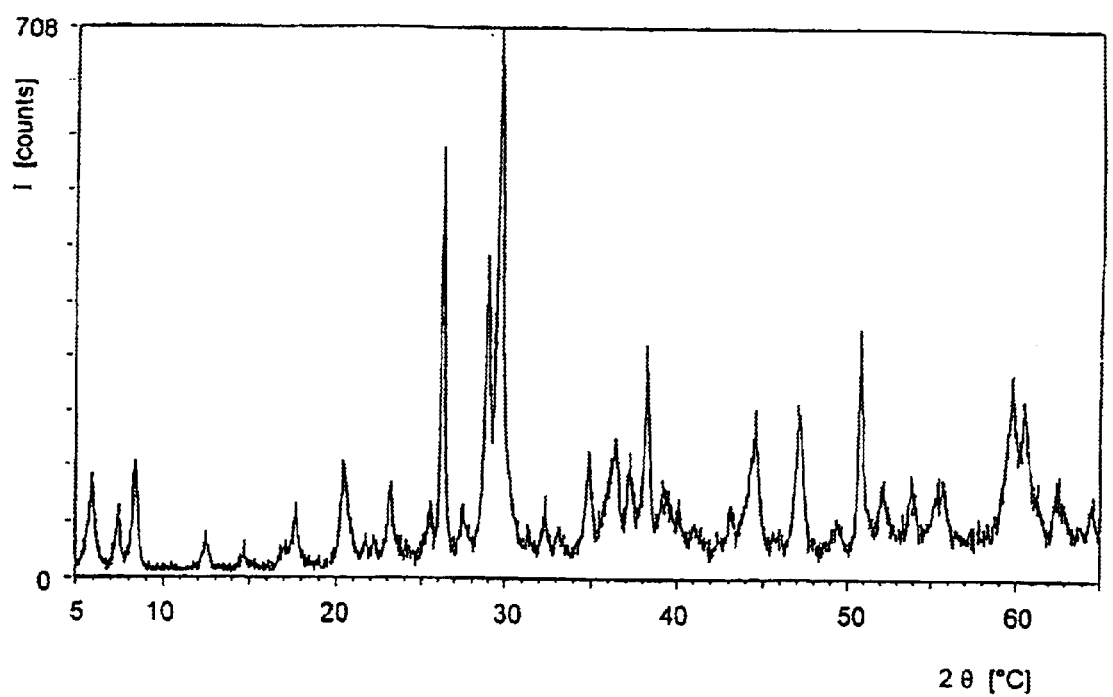

where M is a metal selected from the group consisting of Li, Na, K, Rb, Cs, Tl, Mg, Ca, Sr, Ba, Cu, Zn, Cd, Pb, Cr, Au, Al, Fe, Co, Ni and/or Mo,
a is from 0.3 to 1.9 and
b is from 0 to 0.5, with the proviso that the difference $(a-b) \geq 0.1$ and
c is from 0 to 20 and
x is a number determined by the valence and amount of elements different from oxygen in the formula I,
has a crystal structure giving an X-ray powder diffraction pattern which displays reflections at the lattice spacings d of 15.23±0.6, 12.16±0.4, 10.68±0.3, 3.41±0.04, 3.09±0.04, 3.02±0.04, 2.36±0.04 and 1.80±0.04 Å.

Precatalysts and catalysts produced therefrom for the partial oxidation of aromatic hydrocarbons are also provided.

8 Claims, 2 Drawing Sheets

SILVER- AND VANADIUM-CONTAINING MULTIMETAL OXIDE AND ITS USE

The present invention relates to a multimetal oxide of the formula I $$Ag_{a-b}M_bV_2O_x \cdot c\, H_2O, \quad \text{I}$$

where M is a metal selected from the group consisting of Li, Na, K, Rb, Cs, Tl, Mg, Ca, Sr, Ba, Cu, Zn, Cd, Pb, Cr, Au, Al, Fe, Co, Ni and/or Mo,
a is from 0.3 to 1.9 and
b is from 0 to 0.5, with the proviso that the difference $(a-b) \geq 0.1$ and
c is from 0 to 20 and
x is a number determined stochiometrically by the valence and amount of elements different from oxygen in the formula I,
which has a crystal structure giving an X-ray powder diffraction pattern which displays reflections at the lattice spacings d of 15.23±0.6, 12.16±0.4, 10.68±0.3, 3.41±0.04, 3.09±0.04, 3.02±0.04, 2.36±0.04 and 1.80±0.04 Å.

As is known, many carboxylic acids and/or carboxylic anhydrides are prepared industrially by catalytic gas-phase oxidation of aromatic hydrocarbons such as benzene, o-, m- or p-xylene, naphthalene, toluene or durene (1,2,4,5-tetramethylbenzene) in fixed-bed reactors, preferably multitube reactors. Depending on the starting material, this method is used to produce, for example, benzoic acid, maleic anhydride, phthalic anhydride, isophthalic acid, terephthalic acid or pyromellitic anhydride. The customary procedure in such a process is to pass a mixture of a gas comprising molecular oxygen, for example air, and the starting material to be oxidized through a multiplicity of tubes arranged in a reactor, in which tubes a bed of at least one catalyst is located. To regulate the temperature, the tubes are surrounded by a heat transfer medium, for example a salt melt. Despite this thermostatting, hot spots in which the temperature is higher than in the remainder of the catalyst bed can occur.

These hot spots give rise to secondary reactions such as total combustion of the starting material or lead to the formation of undesirable by-products which can be separated from the reaction product only with great difficulty, if at all, for example the formation of phthalide or benzoic acid in the preparation of phthalic anhydride (PA) from o-xylene.

To reduce the intensity of these hot spots, it has become customary in industry to arrange catalysts of differing activity in zones in the catalyst bed, with the less active catalyst generally being located in the fixed bed such that the reaction gas mixture comes into contact with it first, i.e. it is at the gas inlet end of the bed, while the more active catalyst is located toward the gas outlet end of the catalyst bed (DE-A 25 462 68, EP-A 28 64 48, DE-A 29 48 163, EP-A 16 32 31, U.S. Pat. No. 4,665,200). The catalysts of differing activity in the catalyst bed can be exposed to the reaction gas at the same temperature, but the two zones of catalysts of differing activity can also be thermostatted to different reaction temperatures for contact with the reaction gas (DE-A 28 30 765). According to EP-A 16 32 31, a plurality of the measures mentioned can be employed at the same time for achieving the activity structuring described. German Patent Application No. P 19 823 262 describes a variant using a plurality of catalysts in which the activity of the catalysts increases pseudocontinuously from the gas inlet end to the gas outlet end.

To minimize contamination by troublesome color-imparting components such as phthalide or naphthoquinone and thus obtain a PA of good quality and also to avoid contamination of the waste gas by residual xylene or naphthalene, the reaction is carried out at full conversion (i.e. >99.9% conversion based on the starting material used) (K. Towae et al. in Ullmann's Encyclopedia of Industrial Chemistry, Vol. A20, 1992, 181). A comprehensive review of the prior art for the selective oxidation of o-xylene and a description of the process and catalyst production may be found in WO 98/37967 and in K. Towae et. al., loc. cit.

EP-A 256 352 describes a particular process variant for preparing PA, in which o-xylene is first oxidized in the liquid phase using molecular oxygen over a homogeneously dissolved cobalt catalyst to give toluric acid and the toluric acid formed is subsequently oxidized further to PA in the gas phase over a conventional heterogeneous catalyst.

Catalysts which have been found to be useful for these oxidation reactions are coated catalysts in which the catalytically active composition is applied in the form of a shell to a nonporous support material which is generally inert under the reaction conditions, for example quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or a mixture of these support materials. The catalytically active constituents of the catalytically active composition of these coated catalysts are generally titanium dioxide in the form of its anatase modification and vanadium pentoxide. In addition, the catalytically active composition may further comprise small amounts of many other oxidic compounds which, as promoters, influence the activity and selectivity of the catalyst, for example by decreasing or increasing its activity. Examples of such promoters are the alkali metal oxides, in particular lithium, potassium, rubidium and cesium oxide, thallium (I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Promoters which reduce the activity and increase the selectivity are, for example, the alkaline metal oxides, while oxidic phosphorus compounds, in particular phosphorus pentoxide, increase the activity of the catalyst but reduce its selectivity.

EP-A 447 267 concerns a conventional $V_2O_5$—$TiO_2$ (anatase) catalyst for preparing phthalic anhydride; this catalyst can further comprise small amounts of silver in addition to other doping components.

Although the processes for the oxidation of aromatic hydrocarbons to form carboxylic acids and/or carboxylic anhydrides, in particular the oxidation of o-xylene and/or naphthalene to PA, have been studied very intensively for decades, there is still a need for improved catalysts for this purpose.

Silver-vanadium oxide compounds having an atomic Ag/V ratio of <1 are known as silver-vanadium oxide bronzes. These are generally semiconducting or metallically conductive oxidic solids which preferably have layer or tunnel structures in which part of the vanadium is present in reduced form as V(IV) in the $[V_2O_5]_\infty$ host lattice. $\alpha$-$Ag_xV_2O_5$ bronzes have an orthorhombic crystal structure. They comprise partially reduced $[V_2O_5]_\infty$ layers parallel to the (001) plane which comprise edge- and corner-linked $VO_5$ pyramids. The Ag cations are intercalated between the partially reduced $[V_2O_5]_\infty$ layers. The $\beta$-$Ag_xV_2O_5$ bronzes in which x=0.3–0.4 have tunnel structures. The parent $\beta$-$[V_2O_5]_\infty$ host lattice is built up of greatly distorted $VO_6$ octahedra and distorted trigonal-bipyramidal $VO_5$ units with formation of large channels.

The Ag cations are present in the channels of the β-[V$_2$O$_5$]$_∞$ host lattice. In contrast, the idealized structure of the vanadium bronze δ-Ag$_x$V$_2$O$_5$ (x=0.6–0.9) comprises layers of edge-linked VO$_6$ octahedra between which the Ag cations are intercalated.

Further information on the composition and crystal structure of the oxidic bronzes may be found in A. F. Wells, Structural Inorganic Chemistry, Fifth Edition, Clarendon Press, oxford, 1984, pp. 621–625 and in C. N. R. Rao, B. Raveau, Transition Metal Oxides, VCH Publishers, Inc., New York, 1995, pages 176–179. Specific information on the preparation and structure of the Ag$_x$V$_2$O$_5$ bronzes is given in "Gmelin Handbuch der anorganischen Chemie", 8th edition, silver, part B4, System No. 61, Springer-verlag, Berlin-Heidelberg-New York, 1974, pp. 274–277.

EP-A 856490 discloses a specific silver-vanadium oxide and its use as cathode material in electrochemical cells. This silver-vanadium oxide is produced in a solid-state reaction between silver oxide and a vanadium oxide such as V$_2$O$_5$ or V$_6$O$_{13}$, at from 500° C. to 520° C.

The use of silver-vanadium oxide bronzes as oxidation catalyst is also known. Thus, Y. I. Andreikov, A. A. Lyapkin and V. L. Volkov in Neftekhimiya 17, 559 (1977) describe the use of Ag—V$_2$O$_5$ bronzes having an Ag:V$_2$O$_5$ molar ratio of 0.8:1 for the oxidation of toluene to benzaldehyde/ benzoic acid. Here, the selectivity to desired products decreases with increasing conversion. These catalysts are obtained by joint melting of the starting materials silver or silver nitrate and V$_2$O$_5$ at 750° C., giving a 3-phase mixture which, owing to its method of preparation, has a low BET surface area. In addition, these catalysts may further comprise copper. In RU patent 2088 567, Y. I. Andreikov et al. use Ag—V$_2$O$_5$ bronzes of the above composition on various support materials for the oxidation of toluene to benzaldehyde and benzoic acid. According to the examples, the highest conversion is obtained when using a catalyst comprising the Ag—V$_2$O$_5$ bronze in the form of a shell on a silicon nitride support material. Here, the conversion of toluene into benzaldehyde and benzoic acid at 420° C. is, overall, less than 15%. These catalysts are therefore not economical in operation.

Furthermore, E. I. Andreikov and V. Volkov in Kinet. Katal. 22, 963 (1981) and 22, 1207 (1981) describe the selective oxidation of o-xylene or naphthalene using Ag—V$_2$O$_5$ bronzes having an Ag:V$_2$O$_5$ molar ratio of 0–1:1, with a maximum in respect of activity/selectivity occurring in the range 0.5–0.86:1. In this reaction too, the desired product selectivity decreases with increasing conversion. The catalysts described in these publications are likewise obtained by joint melting of the starting materials.

In addition, JP-A 46-42883 (1971) discloses the oxidation of o-xylene to phthalic anhydride using Ag—VzO$_5$-containing catalysts having an Ag:V$_2$O$_5$ molar ratio of 0.01–1:1 with addition of Tl in a. Tl:V$_2$O$_5$ molar ratio of 0.01–1:1. Although high conversions are achieved using this system, the desired product selectivity and yield are unsatisfactory. These catalysts are produced by impregnation of the support material and subsequent drying and calcination.

JP-A 44-29045 (1969) describes the oxidation of isobutene to methacrolein by means of silver vanadate catalysts in which the Ag/V atomic ratio is $\geq 1$.

Finally, the partial gas-phase oxidation of toluene using silver-vanadium oxide bronzes is known from U.S. Pat. No. 3,485,876, DE-A 12 94 951 and U.S. Pat. No. 4,137,259. The Ag:V atomic ratio in these catalysts is 1:1. The partial gas-phase oxidation of cyclopentadiene over Ag—V$_2$O$_5$ (with a V:Ag atomic ratio of 1:0.003) is likewise known (K.-W. Jun et al., Appl. Catal 63, 267–278 (1990)), where the Ag—V$_2$O$_5$ catalysts contain only V$_2$O$_5$ and no other identifiable solid phases. The selective oxidation of noncyclic, unsaturated hydrocarbons, in particular the oxidation of 1,3-butadiene to furan, with the aid of silver vanadates is described in DE-A 19705326.

In all cases, the selectivity and yield for producing the desired products was unsatisfactory, so that industrial use of the silver-vanadium oxide bronzes was of no economic interest.

It is an object of the present invention to provide novel catalysts and starting compounds for producing them for processes for the oxidation of aromatic hydrocarbons and also processes for producing these catalysts and starting compounds for these catalysts. These catalysts should have improved properties in respect of activity and selectivity in the oxidation of aromatic hydrocarbons to carboxylic acids or carboxylic anhydrides, particularly in the oxidation of o-xylene and/or naphthalene to give phthalic anhydride, compared to known catalysts based on Ag—V$_2$O$_5$.

We have found that this object is achieved by multimetal oxides of the formula I

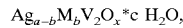

$$Ag_{a-b}M_bV_2O_x \cdot c\, H_2O, \qquad \qquad I$$

where M is a metal selected from the group consisting of Li, Na, K, Rb, Cs, Ti, Mg, Ca, Sr, Ba, Cu, Zn, Cd, Pb, Cr, Au, Al, Fe, Co, Ni and/or Mo, a is from 0.3 to 1.9 and b is from 0 to 0.5, with the proviso that the difference (a–b) $\geq 0.1$ and c is from 0 to 20 and x is a number determined by the valence and amount of elements different from oxygen in the formula I, which have a crystal structure giving an X-ray powder diffraction pattern which displays reflections at the lattice spacings d of 15.23±0.6, 12.16±0.4, 10.68±0.3, 3.41±0.04, 3.09±0.04, 3.02±0.04, 2.36±0.04 and 1.80±0.04 Å, and also by a process for producing them.

Furthermore, we have found precatalysts for producing coated catalysts for the gas-phase partial oxidation of aromatic hydrocarbons by means of a gas comprising molecular oxygen, comprising an inert, nonporous support material and one or more layers applied thereto in the form of a shell, where this/these shell-like layer or layers comprises/comprise from 30 to 100% by weight, based on the total weight of this layer or layers, of an abovementioned multimetal oxide, and also coated catalysts for the gas-phase partial oxidation of aromatic hydrocarbons obtainable, for example, from these precatalysts or the multimetal oxides of the invention and comprising an inert, nonporous support material and, applied thereto one or more layer or layers comprising a catalytically active composition which comprises, based on its total weight, from 30 to 100% by weight of one or more silver-vanadium oxide bronzes having an Ag:V atomic ratio of from 0.15 to 0.95 and has a BET surface area of from 2 to 100 m$^2$/g.

We have also found a process for preparing carboxylic acids and/or carboxylic anhydrides by partial oxidation of aromatic compounds, in particular of o-xylene or naphthalene or mixtures of these compounds or of toluene in the gas phase by means of a gas comprising molecular oxygen at elevated temperature over a catalyst whose catalytically active composition is applied in the form of a shell to an inert, nonporous support material, wherein the catalyst used is a coated catalyst whose catalytically active composition, based on its total weight, comprises from 30 to 100% by weight of a silver-vanadium oxide bronze having an Ag:V atomic ratio of from 0.15 to 0.95 and has a BET surface area of from 2 to 100 m²/g, in the presence or absence of at least one coated catalyst for the oxidation of aromatic hydrocarbons to carboxylic acids and/or carboxylic anhydrides which is different from the above described coated catalyst and whose catalytically active composition comprises vanadium pentoxide and anatase as significant catalytically active constituents and, if such a second coated catalyst is present, it is used in a combined catalyst bed with the coated catalyst of the above composition in the oxidation reactor.

In the present application, the X-ray reflections are reported in the form of the lattice spacings d[Å] which are independent of the wavelength of the X-rays used and can be calculated from the measured angle of the diffraction by means of the Bragg equation.

In general, the complete X-ray powder diffraction pattern of the novel multimedia oxide of the formula I includes inter alia the 17 reflections listed in Table 1. Less intense reflections in the X-ray powder diffraction pattern of the novel multimetal oxides of the formula I have been disregarded in Table 1.

TABLE 1

| Reflection | d [Å] |
|---|---|
| 1 | 15.23 ± 0.6 |
| 2 | 12.16 ± 0.4 |
| 3 | 10.68 ± 0.3 |
| 4 | 5.06 ± 0.06 |
| 5 | 4.37 ± 0.04 |
| 6 | 3.86 ± 0.04 |
| 7 | 3.41 ± 0.04 |
| 8 | 3.09 ± 0.04 |
| 9 | 3.02 ± 0.04 |
| 10 | 2.58 ± 0.04 |
| 11 | 2.48 ± 0.04 |
| 12 | 2.42 ± 0.04 |
| 13 | 2.36 ± 0.04 |
| 14 | 2.04 ± 0.04 |
| 15 | 1.93 ± 0.04 |
| 16 | 1.80 ± 0.04 |
| 17 | 1.55 ± 0.04 |

Depending on the degree of crystallinity and the texturing of the resulting crystals of the multimetal oxide of the invention, there can be, however, a weakening of the intensity of the reflections in the X-ray powder pattern which can go so far that some relatively low-intensity reflections are no longer detectable in the X-ray powder pattern, without it having an adverse effect on the properties of the precatalysts and catalysts produced from the multimetal oxide of the invention. The absence of some relatively low-intensity reflections in the X-ray powder pattern of a multimetal oxide of the chemical composition given by formula I therefore does not mean that the multimetal oxide is not according to the present invention; on the other hand, the presence of all 17 reflections in the X-ray powder pattern indicates that the multimetal oxide in question is a multimetal oxide according to the present invention of particularly high crystallinity. A high degree of crystallinity of the multimetal oxides of the present invention may have an advantageous effect on its processing properties in the production of the precatalysts and catalysts of the present invention. It will be obvious to those skilled in the art that mixtures of the multimetal oxides of the present invention with other crystalline compounds will display additional reflections. Such mixtures of the multimetal oxide with other crystalline compounds can be prepared in a targeted way by mixing the multimetal oxide of the present invention with such compounds or can be formed in the preparation of the multimetal oxides of the present invention by incomplete reaction of the starting materials.

The reflections 1 to 17 shown in Table 1 generally have the approximate relative intensities given in Table 2 ($I_{rel}$ [%]):

TABLE 2

| Reflection | $I_{rel}$ [%] |
|---|---|
| 1 | 16 |
| 2 | 11 |
| 3 | 18 |
| 4 | 11 |
| 5 | 23 |
| 6 | 16 |
| 7 | 80 |
| 8 | 61 |
| 9 | 100 |
| 10 | 23 |
| 11 | 24 |
| 12 | 23 |
| 13 | 38 |
| 14 | 26 |
| 15 | 31 |
| 16 | 43 |
| 17 | 36 |

As indicated by the above discussion of the intensity of the reflections, the 17 intensity values given in Table 2 can vary in terms of their ratios to one another.

In the multimetal oxide of the formula I, the value of the variable a can be from 0.3 to 1.9, preferably from 0.5 to 1.0 and particularly preferably from 0.6 to 0.9, and the value of the variable b can be from 0 to 0.5, preferably from 0 to 0.3 and in particular from 0 to 0.1, provided that the difference (a−b) is greater than or equal to 0.1. The number x is determined by the valence and amount of the elements other than oxygen in the multimetal oxide of the formula I. The number c, which is a measure of the water content, can be from 0 to 20, preferably from 0 to 5, in particular from 0 to 1.

Particularly suitable multimetal oxides of the formula I have a composition of the formula

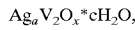

$Ag_aV_2O_x*cH_2O$, where a is from 0.6 to 0.9, the value of the variable x is determined by the amount and valence of the silver and vanadium component and c is from 0 to 5.

The multimetal oxides of the present invention are new chemical compounds.

The new multimetal oxides generally have a fibrous crystal morphology, with the mean ratio of fiber diameter to fiber length being<0.6, preferably <0.3 and particularly preferably <0.1, where this ratio is, of course, always>0. The specific surface area determined by the BET method and measured in accordance with DIN 66 131, which is based on the "Recommendations 1984" of the IUPAC International Union of Pure and Applied Chemistry (cf. Pure & Appl. Chem. 57, 603 (1985)), is generally more than 1 m²/g, preferably from 3 to 250 m²/g, in particular from 10 to 250 m²/g and particularly preferably from 20 to 80 m²/g.

As metals M, the metals Li, Na, X, Rb, Cs, Tl, Mg, Ca, Sr, Ba, Cu, Zn, Cd, Pb, Cr, Au, Al, Fe, Co, Ni and/or Mo can be constituents of the multimetal oxides of the present invention. Preference is given to Na, K, Rb, Tl, Au and Cu.

To prepare the multimetal oxides of the present invention, the usual procedure is to heat a suspension of vanadium pentoxide (V$_2$O$_5$) with the solution of a silver salt in a solvent and, if desired, a solution of a compound of the metal component M. As solvents for this reaction, it is possible to use polar organic solvents such as polyols, polyethers or amines, e.g. pyridine, but preference is given to using water as solvent. As silver salt, preference is given to using silver nitrate, although the use of other soluble silver salts, e.g. silver acetate, silver perchlorate or silver fluoride, is likewise possible. As salts of the metal component M, it is usual to select those which are soluble in the solvent used. If water is used as solvent in the preparation of the multimetal oxides of the present invention, it is possible to use, for example, the perchlorates or carboxylates, in particular the acetates, of the metal component M; preference is given to using the nitrates of the metal component M concerned.

The reaction of V$_2$O$_5$ with the silver salt and possibly the salt of the metal component M can generally be carried out at room temperature or at elevated temperature. As a rule, the reaction is carried out at from 20 to 375° C., preferably from 20 to 100° C. and particularly preferably from 60 to 100° C. If the temperature of the reaction is above the boiling point of the solvent used, the reaction is advantageously carried out in a pressure vessel at the autogenous pressure of the reaction system. The reaction conditions are preferably selected so that the reaction can be carried out at atmospheric pressure. Depending on the type of starting materials reacted and the temperature conditions employed, the reaction time can be from 10 minutes to 3 days. An extension of the reaction time, for example to 5 days or more, is possible. In general, the reaction of the V$_2$O$_5$ with the silver salt and possibly one or more salts of the metal component M to give the multimetal oxide of the present invention is carried out over a period of from 6 to 24 hours. During the reaction, the orange-red color of the V$_2$O$_5$ suspension changes and the new compound is formed as a dark brown suspension.

Depending on the desired chemical composition of the multimetal oxide of the formula I, it is prepared by reacting the amounts of V$_2$O$_5$, silver salt and, if desired, the salt of the metal component M determined by a and b in formula I. Thus, the silver salt is generally reacted with the vanadium pentoxide in a ratio corresponding to an Ag:V atomic ratio of from 0.15 to 0.95, preferably from 0.25 to 0.5, which corresponds to a value of a in the formula I of from 0.3 to 1.9 or from 0.5 to 1.0. Particularly preferably, the silver salt is added in an amount relative to the vanadium pentoxide corresponding to an Ag:V atomic ratio of from 0.3 to 0.45, which corresponds to a value of a in formula I of from 0.6 to 0.9. After the reaction is complete, the novel multimetal oxide having a fibrous crystal morphology is obtained.

The multimetal oxide of the present invention formed in this way can be isolated from the reaction mixture and stored for future use. The multimetal oxide can be isolated by, for example, filtering the suspension and drying the solid obtained. Drying can be carried out either in conventional dryers or, for example, in freeze dryers. The drying of the multimetal oxide suspension obtained is particularly advantageously carried out by means of spray drying. It may be advantageous to wash the multimetal oxide obtained in the reaction free of salts prior to drying. Spray drying is generally carried out under atmospheric pressure or subatmospheric pressure. The pressure employed and the solvent used determine the inlet temperature of the drying gas, generally air although it is, of course, also possible to use other drying gases such as nitrogen or argon. The temperature at which the drying gas enters the spray dryer is advantageously selected so that the outlet temperature of the drying gas cooled by vaporization of the solvent does not exceed 200° C. for any prolonged time. In general, the outlet temperature of the drying gas is set to from 50 to 150° C., preferably from 100 to 140° C. If storage of the multimetal oxide is not intended, the multimetal oxide suspension obtained can also be passed to the further use, for example for coating the precatalysts of the present invention, without prior isolation and drying of the multimetal oxide.

The multimetal oxides of the present invention are used as precursor compounds for preparing the catalytically active composition of coated catalysts as are used for the gas-phase oxidation of aromatic hydrocarbons to carboxylic acids and/or carboxylic anhydrides by means of a gas comprising molecular oxygen. Multimetal oxides of the formula I which have a fibrous crystal morphology with a mean ratio of fiber diameter to fiber length of less than 0.6, preferably less than 0.3 and particularly preferably less than 0.1, (but always greater than 0) have been found to be particularly advantageous for this purpose. Among these multimetal oxides of fibrous crystal morphology, preference is in turn given, for this purpose, to those whose BET surface area is from 3 to 250 m$^2$/g, in particular from 10 to 250 m$^2$/g and particularly preferably from 20 to 80 m$^2$/g. AS regards their chemical composition, the multimetal oxides of the formula I used for producing the above-mentioned coated catalysts are particularly preferably ones in which a is from 0.6 to 0.9 and b is, disregarding industrially virtually unavoidable and effectively inactive impurities introduced via the starting material used, equal to 0, in particular those of the formula

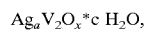

Ag$_a$V$_2$O$_x$*c H$_2$O, where a is from 0.6 to 0.9, c is from 0 to 5 and x is a number determined by the valence and amount of silver and vanadium in this multimetal oxide.

Even if the multimetal oxides of the present invention are preferably used for producing the coated catalysts of the present invention for the oxidation of aromatic hydrocarbons, they can also be used as precursor compounds for producing conventional supported catalysts or unsupported catalysts, i.e. catalysts which contain no support material. A further possible use of the multimetal oxides of the present invention is as cathode material or for producing cathode material for electrochemical cells, for example batteries.

The coated catalysts of the present invention for the partial oxidation of aromatic hydrocarbons to carboxylic acids and/or carboxylic anhydrides are advantageously produced from the multimetal oxides of the present invention via the stage of a "precatalyst" which can be stored and handled as such and from which the coated catalyst of the present invention can be produced either by thermal treatment or in situ in the oxidation reactor under the conditions of the oxidation reaction. The precatalyst is thus a precursor of the finished coated catalyst and comprises a nonporous support material which is inert under the conditions of precatalyst and coated catalyst production and also under the conditions of the partial oxidation of aromatic hydrocarbons to carboxylic acids and/or carboxylic anhydrides and one or more layers applied thereto in the form of a shell, where this shell-like layer or layers of the precatalyst comprises from 30 to 100% by weight, preferably from 50 to 100% by weight, based on the total weight of this layer or layers, of a multimetal oxide of the formula I. The shell-like layer or layers particularly preferably consist(s) entirely of a multimetal oxide of the formula I. If the catalytically active layer or layers further comprise(s) other components in addition to the multimetal oxide of the formula I, these components can be, for example, inert materials of the prior art, e.g. silicon carbide or steatite, or else catalysts for the oxidation of aromatic hydrocarbons to carboxylic acids and/or carboxylic anhydrides which are outside the scope of the present invention and are based on vanadium pentoxide/anatase, as have been mentioned, for example, in the introduction in the discussion of the prior art.

As inert, nonporous support material for the precatalysts and coated catalysts of the present invention, it is possible to use virtually all support materials of the prior art as are advantageously used in the production of coated catalysts for the oxidation of aromatic hydrocarbons to carboxylic acids and/or carboxylic anhydrides, for example quartz ($SiO_2$) porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The expression "nonporous" is used here in the sense of "nonporous except for amounts of pores which have no practical effect", since a small number of pores in a support material which ideally should contain no pores are industrially unavoidable. As advantageous support materials, particular mention may be made of steatite and silicon carbide. The form of the support material is generally not critical for the precatalysts and coated catalysts of the present invention. For example, it is possible to use catalyst supports in the form of spheres, rings, pellets, spirals, tubes, extrudates or granules. The dimensions of these catalyst supports correspond to those of the catalyst supports customarily used for producing coated catalysts for the gas-phase partial oxidation of aromatic hydrocarbons. As stated, the abovementioned support materials can also be mixed in powder form into the catalytically active composition of the coated catalysts of the present invention.

To coat the inert support material with the multimetal oxide of the present invention, it is in principle possible to employ known methods of the prior art. For example, the suspension obtained in the reaction of the vanadium pentoxide with a silver salt and possibly one or more salts of the metal component M can, as in the processes of DE-A 1692938 and DE-A 1769998, be sprayed onto the catalyst support consisting of inert support material in a heated coating drum until the desired amount of multimetal oxide, based on the total weight of the precatalyst, has been applied. In place of coating drums, it is also possible to use as in DE-A 2106796, fluidized-bed coaters as are described in DE-A 1280756 for applying the multimetal oxide of the present invention in the form of a shell to the catalyst support. In place of the suspension obtained in the reaction of the vanadium pentoxide with a silver salt and possibly one or more salts of the metal component M, it is possible and particularly preferred to carry out this coating process using a slurry of the powder of the multimetal oxide of the present invention obtained after isolation and drying. Using a method analogous to that described in EP-A 744214, organic binders, preferably copolymers, can be dissolved in or advantageously added in the form of an aqueous dispersion to the suspension of the multimetal oxide of the present invention as is formed in its preparation or a slurry of a powder of the dried multimetal oxide of the present invention in water, in an organic solvent such as a higher alcohol, a polyhydric alcohol, e.g. ethylene glycol, 1,4-butanediol or glycerol, dimethylformamide, dimethylacetamide, dimethyl sulfoxide, N-methylpyrrolidone or a cyclic urea such as N,N'-dimethylethyleneurea or N,N'-dimethylpropyleneurea or in a mixture of these organic solvents with water, with, in general, binder contents of from 10 to 20% by weight, based on the solids content of the suspension or slurry of the multimetal oxide of the present invention being employed. Suitable binders are, for example, vinyl acetate-vinyl laurate, vinyl acetate-acrylate, styrene-acrylate, vinyl acetate-maleate or vinyl acetate-ethylene copolymers. If organic copolymer polyesters, e.g. those based on acrylate-dicarboxylic anhydride-alkanolamine, in a solution in an organic solvent are added to the slurry of the multimetal oxide of the present invention, the binder content can, similarly to the teachings of the German Patent Application No. P 19823262.4, be reduced to from 1 to 10% by weight, based on the solids content of the suspension or slurry.

In the coating of the catalyst support with the multimetal oxides of the present invention, coating temperatures of from 20 to 500° C. are generally employed, with the coating being able to be carried out in the coating apparatus under atmospheric pressure or subatmospheric pressure. To produce the precatalysts of the present invention, coating is generally carried out at from 0° C. to 200° C., preferably from 20 to 150° C., in particular from room temperature to 100° C. When coating the catalyst support with a moist suspension of the multimetal oxides of the present invention, it can be advantageous to employ higher coating temperatures, e.g. from 200 to 500° C. At the abovementioned lower temperatures, part of any polymeric binder used in the coating process can remain in the layer applied to the catalyst support.

In a future conversion of the precatalyst into a coated catalyst according to the present invention by thermal treatment at from above 200° C. to 500° C., the binder is driven from the applied layer by thermal composition and/or combustion. The conversion of the precatalyst into a coated catalyst according to the present invention can also be carried out by thermal treatment at above 500° C., for example at up to 650° C., and is preferably carried out at from>200° C. to 500° C., in particular from 300 to 450° C.

As will be described in more detail below, the multimetal oxides of the present invention begin to decompose above 200° C., in particular at more than 300° C., to form silver-vanadium oxide bronzes which are the constituents of the catalytically active composition of the coated catalysts of the present invention. Accordingly, at coating temperatures above 200° C., depending in each case on the conditions employed, part of the multimetal oxides of the present invention applied to the catalyst support may decompose to form catalytically active silver-vanadium oxide bronzes and/or silver-vanadium oxide compounds whose structure has not been elucidated crystallographically and which can be converted into said silver-vanadium oxide bronzes. However, this decomposition occurs very slowly in this temperature range, so that in the case of the catalyst supports which have been coated in the range from >200 to 300° C. the applied layer consists essentially of the multimetal oxide of the present invention, as can be established by X-ray crystallographic analysis of a sample abraded from the applied layer. At coating temperatures of from 300 to 500° C., this decomposition proceeds virtually to completion, so that in a coating process at from 300 to 500° C. the coated catalyst of the present invention can be obtained without going through the intermediate of the precatalyst. If the catalyst support is coated with the multimetal oxides of the present invention in the temperature range from above 200° C. to 300° C., the applied layer generally comprises, depending on the type of multimetal oxide used and the time required for carrying out the coating step, varying amounts both of the multimetal oxide of the present invention and the silver-vanadium oxide bronzes and/or silver-vanadium oxide compounds whose structure has not been elucidated crystallographically formed by their partial decomposition.

In principle, any of the abovementioned coating methods can be employed for producing the precatalysts of the present invention and the coated catalysts of the present invention. However, particularly advantageous precatalysts and coated catalysts are obtained if the precatalysts of the present invention are produced, taking into account the above statements, by a method analogous to the catalyst production processes of EP-A 714700 and WO 98/37967 by coating the inert catalyst support with a, preferably spray-dried, powder of the multimetal oxide of the present invention, particularly preferably with a multimetal oxide having the abovementioned advantageous properties in respect of its BET surface area, crystal morphology and chemical composition, at from 0° C. to 200° C., preferably from 20 to 150° C., in particular from room temperature to 100° C., with or without addition of one of the abovementioned binders.

The X-ray powder diffraction pattern of samples of material abraded from these precatalysts produced according to the present invention from the multimetal oxide of the formula I displays, inter alia, reflections at the lattice spacings d as have been specified above in Table 1 for the multimetal oxides of the present invention.

The coated catalysts of the present invention are preferably produced from the precatalysts of the present invention or produced in situ from these precatalysts in the reactor for the oxidation of the aromatic hydrocarbons.

In the thermal treatment of the precatalysts of the present invention at from>200 to 650° C., preferably>250° C. to 500° C., in particular from 300 to 450° C., these precatalysts are converted into the coated catalysts of the present invention for the gas-phase oxidation of aromatic hydrocarbons to carboxylic acids and/or carboxylic anhydrides. In this heat treatment, the multimetal oxide or possibly oxides according to the invention present in the precatalyst decompose(s) at the end into previously known and characterized silver-vanadium oxide bronzes (cf. Bull. Soc. Chim. France 3817, 1967). This can be established by means of x-ray diffraction patterns of samples of material abraded from the catalytically active layer of the novel coated catalysts obtained by means of said thermal treatment of the precatalyst. This conversion of the multimetal oxides of the present invention present in the precatalyst to form known silver-vanadium oxide bronzes in particular also takes place in situ in the reactor for the gas-phase partial oxidation of aromatic hydrocarbons to carboxylic acids and/or carboxylic anhydrides, for example in the reactor for preparing phthalic anhydride from o-xylene and/or naphthalene, at the temperatures of from 300 to 450° C. which are generally employed, if a precatalyst according to the present invention is used in this reaction in place of the coated catalyst of the present invention. In this case, a steady increase in the activity of the coated catalyst is generally observed until completion of the conversion of the multimetal oxide of the present invention into the known silver-vanadium oxide bronzes. The silver-vanadium oxide bronzes formed in this way are thus a catalytically active constituent of the catalytically active layer of the coated catalyst of the present invention.

The thermal conversion of the multimetal oxides of the present invention into silver-vanadium oxide bronzes proceeds via a series of reduction and oxidation reactions which are not yet understood individually. It has been found that, depending on the composition of the atmosphere in which this conversion is carried out in respect of oxygen, inert gases or reducing gases and on the temperature employed, and also depending on whether or not the precatalyst contains an organic binder and on the type and amount of this binder, the thermal treatment of the precatalyst or the coating of the support material at elevated temperature can result in conversion of the multimetal oxides of the present invention first into silver-vanadium oxide compounds which are different from the abovementioned silver-vanadium oxide bronzes and whose crystallographic structure has not been elucidated but which are converted in the reactor under the conditions of the process for oxidizing aromatic hydrocarbons to carboxylic anhydrides and/or carboxylic acids into the above-mentioned silver-vanadium oxide bronzes having the above-mentioned properties, as can be established from the X-ray diffraction patterns of samples abraded from catalysts removed from the reactor. On the basis of present-day knowledge, this process is reversible, i.e. the silver-vanadium oxide bronze present in the catalytically active composition of the coated catalyst of the present invention can, for example, be converted under oxidizing conditions after its removal from the reactor into another silver-vanadium oxide compound which is reduced back to the silver-vanadium oxide bronze concerned after the catalyst has again been installed in the reactor.

In the production of the coated catalyst of the present invention by coating an inert, nonporous catalyst support with the multimetal oxide of the present invention at from>200 to 500° C. or by thermal treatment of the precatalysts of the present invention at from>200 to 650° C., this means that the generation of the catalytically active composition comprising the silver-vanadium oxide bronze can be carried out in one or more stages. The single-stage generation of the silver-vanadium oxide bronze in the catalytically active layer of the coated catalyst of the present invention is preferably carried out by treating the precatalyst of the present invention in situ in the oxidation reactor under the conditions of the oxidation of aromatic hydrocarbons to carboxylic anhydrides and/or carboxylic acids. However, the single-stage generation of the silver-vanadium oxide bronze in the catalytically active layer of the coated catalysts of the present invention can also be carried out outside the oxidation reactor, for example during the coating of the support material with the multimetal oxide of the present invention at from>200° C. to 500° C. or a separate thermal treatment at from>200 to 650° C. of the precatalyst coated with the multimetal oxide at from 0° C. to 200° C.; in this procedure, the above-mentioned influencing parameters such as the composition of the gas atmosphere, the presence or absence of a binder and also the type and amount of the binder have to be taken into account. In such a procedure, the optimum conditions for generating the silver-vanadium oxide bronze in the catalytically active layer of the coated catalyst of the present invention are advantageously determined in each individual case by means of a preliminary experiment.

There are a number of procedures available for the multistage generation of the silver-vanadium oxide bronze in the catalytically active layer of the coated catalysts of the present invention. For example, a precatalyst coated at from 0 to 200° C. with the multimetal oxide of the present invention can be subjected to a thermal treatment at from >200 to 650° C. under conditions which have not been optimized for the generation of the silver-vanadium oxide bronze, so that the multimetal oxide forms the abovementioned silver-vanadium oxide compounds whose crystallographic structure has not been elucidated which are subsequently, i.e. in a second stage, converted in situ in the oxidation reactor for the oxidation of aromatic hydrocarbons to carboxylic anhydrides and/or carboxylic acids into the desired, catalytically active silver-vanadium oxide bronzes under the conditions of this oxidation. It is also possible, for example, to coat the catalyst support with the multimetal oxide of the present invention at from>200° C. to 500° C. under conditions which have not been optimized for the formation of the silver-vanadium oxide bronze, so that not precisely definable silver-vanadium oxide compounds are formed from the multimetal oxide during the coating process and to convert the resulting coated support, if desired after a further thermal treatment at from>200 to 650° C., into a coated catalyst according to the present invention in situ in the oxidation reactor for the oxidation of aromatic hydrocarbons to carboxylic anhydrides and/or carboxylic acids under the conditions of this oxidation.

Another possible way of producing a coated catalyst according to the present invention is to treat the multimetal oxide powder of the present invention thermally at from>200° C. to 650° C. and to coat the inert, nonporous catalyst support, if desired with addition of a binder, with the resulting silver-vanadium oxide bronze or the abovementioned silver-vanadium oxide compounds whose structure has not been elucidated crystallographically. If the catalyst support is coated with the silver-vanadium oxide bronze obtained, this produces a coated catalyst according to the present invention; if the catalyst support is coated with the abovementioned silver-vanadium oxide compounds whose structure has not been elucidated crystallographically and may be obtained, the coated catalyst support is preferably converted in situ in the oxidation reactor into a coated catalyst according to the present invention under the conditions of the oxidation of aromatic hydrocarbons to carboxylic anhydrides and/or carboxylic acids.

The coated catalysts of the present invention are, however, particularly preferably produced from the precatalysts of the present invention in a single stage or, if desired after thermal treatment during the course of or after coating of the catalyst support, in a plurality of stages, in particular in a single stage, in each case in situ in the oxidation reactor under the conditions of the oxidation of aromatic hydrocarbons to carboxylic anhydrides and/or carboxylic acids.

The catalytically active shell of the coated catalyst produced according to the present invention generally comprises from 30 to 100% by weight, preferably from 50 to 100% by weight, based on the total weight of the catalytically active shell, of the silver-vanadium oxide bronzes produced in this way, with the silver and the vanadium generally being present in the catalytically active shell in Ag:V atomic ratio of from 0.15 to 0.95, preferably from 0.25 to 0.5 and particularly preferably from 0.3 to 0.45. The catalytically active layer of the coated catalysts of the present invention particularly preferably consists entirely of the silver-vanadium oxide bronzes produced according to the present invention. If the catalytically active layer or layers further comprise(s) other components in addition to the silver-vanadium oxide bronzes produced according to the present invention, these can be, for example, inert materials of the prior art, e.g. silicon carbide or steatite, or else catalyst compounds for the oxidation of aromatic hydrocarbons to carboxylic acids and/or carboxylic anhydrides which are outside the scope of the present invention, for example ones based on vanadium pentoxide/anatase, as have been mentioned by way of example in the introduction in the discussion of the prior art. The thickness of the catalyst shell comprising the catalytically active constituents is generally from 10 to 250 μm. This also applies if the catalyst shell consists of a plurality of layers applied in succession.

Surprisingly, despite similar X-ray diffraction patterns, the coated catalysts of the present invention have improved properties in the oxidation of aromatic hydrocarbons to carboxylic acids and/or carboxylic anhydrides compared to catalysts of the prior art based on silver-vanadium oxide (e.g. E. I. Andreikov; V. Volkov; Kinet. Katal. 22, 963 (1981) and Kinet. Katal. 22, 1207 (1981)). This is presumably attributable to the higher, compared to the prior art, BET surface area of the coated catalysts of the present invention which is generally from 2 to 100 $m^2/g$, preferably from 2 to 40 $m^2/g$ and particularly preferably from 3 to 20 $m^2/g$, and is thus a number of times that which can be achieved according to the prior art. The use of the multimetal oxides of the present invention for producing the coated catalyst, preferably via the precatalyst stage, obviously leads to a greater BET surface area of the catalytically active silver-vanadium oxide bronzes produced therefrom.

The coated catalysts of the present invention are used for the partial oxidation of aromatic hydrocarbons to carboxylic acids and/or carboxylic anhydrides, in particular for the gas-phase partial oxidation of o-xylene and/or naphthalene to give phthalic anhydride or of toluene to give benzoic acid and benzaldehyde, by means of a gas comprising molecular oxygen. For this purpose, the catalysts of the present invention can be used alone or in combination with other catalysts having different activities, for example catalysts of the prior art based on vanadium oxide/anatase, in which case the different catalysts are generally located in the reactor in separate catalysts beds which may be arranged in one or more fixed catalyst beds.

The coated catalysts or precatalysts of the present invention are, for this purpose, introduced into the reaction tubes of a tube reactor, which tubes are thermostatted from the outside, e.g. by means of a salt melt, to the reaction temperature. If a precatalyst according to the present invention is used in place of the coated catalyst of the present invention, it is converted under the temperature conditions of the partial oxidation of aromatic hydrocarbons to carboxylic acids and/or carboxylic anhydrides, in particular the partial oxidation of o-xylene and/or naphthalene to PA or the partial oxidation of toluene to benzoic acid and benzaldehyde, into a coated catalyst according to the present invention. The reaction gas is passed over the catalyst bed prepared in this way at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, at a space velocity of generally from 750 to 5000 $h^{-1}$.

The reaction gas fed to the catalyst is generally produced by mixing a gas comprising molecular oxygen and, if desired, suitable reaction moderators and/or diluents such as steam, carbon dioxide and/or nitrogen with the aromatic hydrocarbon to be oxidized. The gas comprising molecular oxygen generally comprises from 1 to 100% by volume, preferably from 2 to 50% by volume and particularly preferably from 10 to 30% by volume, of oxygen, from 0 to 30% by volume, preferably from 0 to 10% by volume, of water vapor and from 0 to 50% by volume, preferably from 0 to 1% by volume, of carbon dioxide, with the balance being nitrogen. To produce the reaction gas, the gas comprising molecular oxygen is generally mixed with from 30 to 300 g of the aromatic hydrocarbon to be oxidized per standard $m^3$ of gas, preferably from 70 to 150 g per standard $m^3$ of gas. Air is particularly advantageously used as the gas comprising molecular oxygen.

The gas-phase partial oxidation is advantageously carried out using two or more zones, preferably two zones, of the catalyst bed present in the reaction tube which are thermostatted to different reaction temperatures; for this purpose it is possible to employ, for example, reactors with separate salt baths, as described in DE-A 22 01 528 or DE-A 28 30 765. If the reaction is carried out in two reaction zones, as described in DE-A 40 13 051, the reaction zone nearest the gas inlet for the reaction zone, which zone generally makes up from 30 to 80% by volume of the total catalyst volume, is generally thermostatted to a reaction temperature which is from 1 to 200° C., preferably from 1 to 10° C. and in particular from 2 to 8° C., higher than that in the reaction zone nearest the gas outlet. Such a mode of operation is referred to as two-zone or multizone structuring of the reactor. Alternatively, the gas-phase oxidation can also be carried out at a uniform reaction temperature without division into temperature zones.

In a preferred embodiment of the process for the partial oxidation of aromatic hydrocarbons to carboxylic acids and/or carboxylic anhydrides, which is found to be particularly advantageous for the preparation of phthalic anhydride from o-xylene and/or naphthalene, the aromatic hydrocarbon, e.g. o-xylene, is first reacted over a bed of the coated catalyst of the present invention to convert it partially into phthalic anhydride and other oxidation products such as o-tolualdehyde, o-toluic acid and phthalide. The resulting product mixture, which further comprises unreacted o-xylene, can then be processed further by, as alternatives, either a) separating the o-xylene from the phthalic anhydride and the other abovementioned oxidation products which are intermediates on the reaction path from o-xylene to phthalic anhydride and recirculating it and feeding the stream comprising phthalic anhydride and intermediates to one or more further catalyst beds comprising, for example, a coated catalyst based on vanadium oxide/anatase where the intermediates are oxidized selectively to form phthalic anhydride; or b) passing the product mixture without further work-up, i.e. without separation of o-xylene, over a second catalyst bed or, if desired, over further catalyst beds as can be used according to the prior art for preparing phthalic anhydride from o-xylene, e.g. coated catalysts based on vanadium oxide/anatase as catalytically active constituents. This can be achieved using two-zone or multizone structuring in the same reactor or using an after-reactor.

This way of carrying out the reaction achieves, overall, a significantly higher phthalic anhydride yield than when using catalysts of the prior art alone, since the coated catalysts of the present invention can oxidize o-xylene and/or naphthalene significantly more selectively to form phthalic anhydride or the abovementioned intermediates than is possible when using only catalyst systems based on vanadium oxide/anatase according to the prior art. In addition, the abovementioned combination of catalyst beds comprising the coated catalyst of the present invention in the first reaction zone and one or more [lacuna] comprising coated catalysts based on vanadium oxide/anatase makes possible the complete conversion of the o-xylene used together with a high selectivity for the formation of phthalic anhydride of high product quality.

The oxidation of toluene to benzoic acid can be carried out analogously, with a mixture of unreacted toluene, benzoic acid and benzaldehyde being formed initially. Alternatively, if desired, it is possible to isolate the by-product benzaldehyde which is likewise a valuable product and is used, for example, as a flavor.

EXAMPLE 1

Preparation of $HNO_3$-Containing $Ag_{0.73}V_2O_x$ 90.95 g of $V_2O_5$ (=0.5 mol) were added while stirring to 7 l of deionized water at 60° C. An aqueous solution of 62.0 g of $AgNO_3$ (=0.365 mol) in 1 l of water was added while continuing to stir to the orange suspension obtained. Subsequently, the temperature of the resulting suspension was increased to 90° C. over a period of 2 hours and the mixture was stirred at this temperature for 24 hours. The dark brown suspension obtained was then cooled and spray dried (inlet temperature (air)=380° C., outlet temperature (air)=104° C.).

The powder obtained had a specific surface area determined by the BET method of 45.0 $m^2/g$. Chemical analysis gave an Ag/v atomic ratio of 0.38. An X-ray powder pattern of the powder obtained was recorded by means of a Siemens diffractometer D 5000 using Cu $K_\alpha$ radiation (40 kV, 30 mA). The diffractometer was equipped with an automatic primary and secondary diaphragm system and a secondary monochromator and scintillation detector. Table 3 shows the X-ray powder pattern measured on the powder obtained in the 2θ range from 5 to 65° reported as lattice spacings d [Å] which are independent of the wavelength of the X-rays used and also the associated relative intensities $I_{rel}[\%]$, based on the most intense reflection, of the various reflections. The relative intensities were determined from the peak heights of the reflections.

TABLE 3

| d [Å] | $I_{rel}$ [%] |
|---|---|
| 15.23 | 16 |
| 12.16 | 11 |
| 10.68 | 18 |
| 7.16 | 6 |
| 6.10 | 5 |
| 5.24 | 5 |
| 5.06 | 11 |
| 4.37 | 23 |
| 4.12 | 7 |
| 4.02 | 8 |
| 3.86 | 16 |
| 3.51 | 14 |
| 3.41 | 80 |
| 3.26 | 13 |
| 3.09 | 61 |
| 3.02 | 100 |
| 2.78 | 13 |
| 2.71 | 10 |
| 2.58 | 23 |
| 2.50 | 21 |
| 2.48 | 24 |
| 2.42 | 23 |
| 2.36 | 38 |
| 2.30 | 17 |
| 2.25 | 14 |
| 2.10 | 13 |
| 2.04 | 26 |
| 1.93 | 31 |
| 1.85 | 13 |
| 1.80 | 43 |
| 1.76 | 19 |
| 1.70 | 18 |
| 1.55 | 36 |
| 1.53 | 33 |
| 1.49 | 17 |
| 1.44 | 14 |

For comparison, the corresponding literature data for β-$Ag_{0.35}V_2O_5$ and δ-$Ag_{0.8}V_2O_5$ (from: A. Casalot, M. Pouchard: Bull. Soc. Chim. France 3817 (1967); Table III) are shown in Table 4 below.

TABLE 4

| β-Ag$_{0.35}$V$_2$O$_5$ | | δ-Ag$_{0.80}$V$_2$O$_5$ | |
|---|---|---|---|
| d (Å) | I/I$_o$ | d (Å) | I/I$_o$ |
| 7.20 | 12 | 4.85 | 20 |
| 6.96 | 8 | 4.38 | 2 |
| 4.72 | 40 | 3.507 | 24 |
| 3.83 | 40 | 3.232 | 72 |
| 3.497 | 12 | 2.910 | 100 |
| 3.367 | 20 | 2.768 | 40 |
| 3.045 | 100 | 2.544 | 32 |
| 2.910 | 55 | 2.418 | 16 |
| 2.887 | 50 | 2.270 | 2 |
| 2.720 | 38 | 2.241 | 2 |
| 2.616 | 16 | 2.189 | 4 |
| 2.443 | 12 | 1.967 | 4 |
| 2.363 | 12 | 1.945 | 8 |
| 2.164 | 17 | 1.916 | 3 |
| 1.971 | 25 | 1.855 | 16 |
| 1.861 | 12 | 1.828 | 24 |
| 1.802 | 30 | 1.754 | 6 |

EXAMPLE 2

Preparation of Nitrate-Free Ag$_{0.73}$V$_2$O$_x$

The dark brown suspension obtained as described in Example 1 was filtered with suction and the solid was washed with 7 l of water. The filtrate obtained at the end was virtually silver-free. The dark brown filter cake obtained was dried for 15 hours at 110° C. in a vacuum drying oven.

The powder obtained had a specific surface area determined by the BET method of 47.5 m$^2$/g. Chemical analysis gave an Ag/V atomic ratio of 0.34. Potentiometric determination of the oxidation state of the vanadium component in the powder obtained showed the presence of very predominantly vanadium (V) (37.7% by weight) together with very little vanadium (IV) (0.2% by weight). As examination by scanning electron microscopy shows, the powder obtained has a fibrous morphology. The X-ray powder diffraction pattern agreed with that of the product from Example 1. The X-ray powder diffraction pattern is shown in FIG. 1.

EXAMPLE 3

Production of the Comparative Catalysts

Comparative Catalyst (a)

50.0 kg of steatite (magnesium silicate) rings having an external diameter of 8 mm, a length of 6 mm and a wall thickness of 1.5 mm were heated to 160° C. in a coating drum and sprayed with a suspension of 25.0 kg of anatase having a BET surface area of 20 m$^2$/g, 1.81 kg of vanadyl oxalate, 0.143 kg of cesium sulfate, 38 kg of water and 9.85 kg of formamide until the weight of the layer applied in this way was 10.0% of the total weight (after calcination at 450° C.; for this determination, samples are taken from the coating drum at various times and calcined at 450° C.) of the finished coated catalyst. The catalytically active composition applied in this way, i.e. the catalyst shell, comprised 0.40% by weight of cesium (calculated as Cs), 4.0% by weight of vanadium (calculated as V$_2$O$_5$) and 95.6% by weight of titanium dioxide (calculated as TiO$_2$).

Comparative Catalyst (b)

50 kg of steatite (magnesium silicate) rings having an external diameter of 8 mm, a length of 6 mm and a wall thickness of 1.5 mm were heated to 160° C. in a coating drum and sprayed with a suspension of 28.6 kg of anatase having a BET surface area of 20 m$^2$/g, 4.11 kg of vanadyl oxalate, 1.03 kg of antimony trioxide, 0.179 kg of ammonium dihydrogen phosphate, 0.046 kg of cesium sulfate, 44.1 kg of water and 9.14 kg of formamide until the weight of the applied layer was 10.5% of the total weight of the finished catalyst (after calcination at 450° C.). The catalytically active composition applied in this way, i.e. the catalyst shell, comprised 0.15% by weight of phosphorus (calculated as P), 7.5% by weight of vanadium (calculated as V$_2$O$_5$), 3.2% by weight of antimony (calculated as Sb$_2$O$_3$), 0.1% by weight of cesium (calculated as Cs) and 89.05% by weight of titanium dioxide (calculated as TiO$_2$).

Catalyst (c) According to the Present Invention "Precatalyst"

The HNO$_3$-containing Ag$_{0.73}$V$_2$O$_x$ powder prepared as described in Example 1 was applied as follows to magnesium silicate rings: 700 g of steatite rings having an external diameter of 8 mm, a length of 6 mm and a wall thickness of 1.5 mm were coated in a coating drum at 20° C. for 20 minutes with 115 g of the HNO$_3$-containing Ag$_{00.73}$V$_2$O$_x$ powder with addition of 56 g of a mixture containing 30% by weight of water and 70% by weight of glycerol and subsequently dried. The weight of the catalytically active composition applied in this way was, after heat treatment at 400° C. for ½ hour, 12.9% by weight, based on the total weight of the finished catalyst. This weight determination was carried out using samples of the precatalyst taken from the coating drum at various times; the precatalyst itself was not heated to 400° C. during its production.

EXAMPLE 4

Preparation of Phthalic Anhydride Using the Comparative Catalyst 3(a) and 3(b))

From the bottom upward, 1.30 m of the catalyst 3b and subsequently 1.60 m of the catalyst 3a were introduced into an iron tube having a length of 3.85 m and an internal diameter of 25 mm. To regulate the temperature, the iron tube was surrounded by a salt melt. 4.0 standard m$^3$/h of air were passed through the tube from the top downward. At loadings with 98.5% purity by weight o-xylene of 60–80 g of o-xylene/standard m$^3$ of air and a salt bath temperature of 352–355° C., an average phthalic anhydride (PA) yield of 113.3% by weight was achieved (yield means the PA obtained in percent by weight, based on 100%-pure o-xylene). The conversion was>99.95% and the residual phthalide content at the reactor outlet was<0.20% by weight.

EXAMPLE 5

Preparation of Phthalic Anhydride Using a Combination of the Precatalyst 3(c) According to the Present Invention with the Known Catalysts 3 (a) and 3(b) in One Tube From the bottom upward, 0.90 m of the catalyst 3(b), 0.80 m of the catalyst 3(a) and subsequently 1.20 m of the precatalyst 3(c) were introduced into an iron tube having a length of 3.85 m and an internal diameter of 25 mm. To regulate the temperature, the iron tube was surrounded by a salt melt. 4.0 standard m$^3$/h of air having loadings of 98.5% purity by weight o-xylene of from 60 to 80 g of o-xylene/ standard m$^3$ of air were passed through the tube from the top downward. At a loading of 60–80 g and a salt bath temperature of 353–358° C., an average PA yield of 115.4% by weight was achieved (yield means the phthalic anhydride obtained in percent by weight, based on 100%-pure o-xylene. The conversion was >99.94% and the residual phthalide content at the reactor outlet was>0.20% by weight.

EXAMPLE 6

Comparison with Ag/$V_2O_5$ Bronze at Partial Conversion a) Production of the Comparative Catalyst 6a A mixture of 90.95 g of $V_2O_5$ (0.5 mol) and 62.0 g of $AgNO_3$ (0.365 mol) was reacted by thermal treatment at 750° C. in air using a method similar to that reported in the literature (E. I. Andreikov, V. L. Volkov, Kin. Katal. 22, 963 (1981)). A melt having the gross composition $Ag_{0.73}V_2O_x$ was formed. The solidified melt was ground to a powder having a particle size distribution of 1–10 μm. An X-ray diffraction pattern of this powder indicated that the comparative Ag—V oxide comprised $Ag_{10.2}V_3O_8$ (main product) and β-Ag—$V_2O_5$ bronze (secondary product). The diffraction lines at d=15.23+0.6, 12.16+0.4, 10.68+0.3, 3.41±0.04, 3.09±0.04, 3.02±0.04, 2.36±0.04 and 1.80±0.04 Å (given in the form of the lattice spacings d [Å] which are independent of the wavelength of the X-rays used) characteristic of the multimetal oxides of the present invention were not found. The powder prepared in this way was applied as follows to magnesium silicate spheres: 700 g of steatite spheres having a diameter of 3.5 mm were coated in a coating drum at 200° C. for 20 minutes with 123.9 g of the $Ag_{0.73}V_2O_x$ powder with addition of 45 g of a mixture containing 70% by weight of water and 30% by weight of glycerol. The weight of the catalytically active composition applied in this way was, after heat treatment for ½ hour at 400° C., 15.0% by weight, based on the total weight of the finished catalyst.

b) Production of the Catalyst 6b According to the Present Invention

Figure 2:
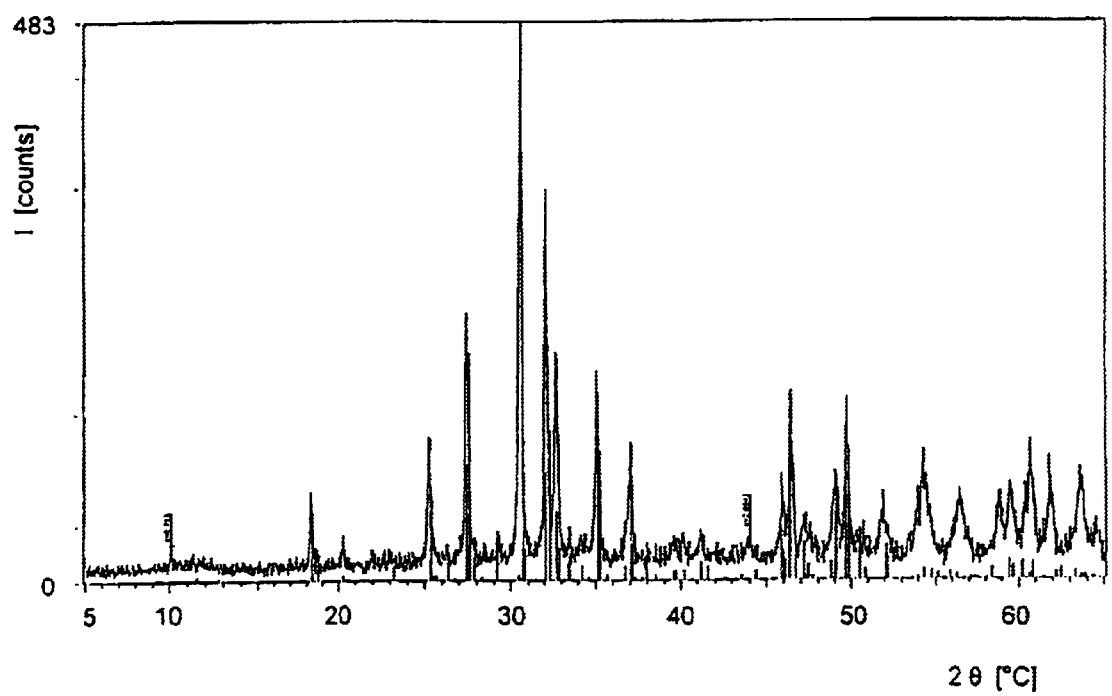

The $HNO_3$-containing $Ag_{0.73}V_2O_x$ powder prepared as described in Example 1 was applied as follows to magnesium silicate spheres: 700 g of steatite spheres having a diameter of 3.5 mm were coated in a coating drum at 20° C. for 20 minutes with 135.9 g of the powder from Example 1 with addition of 62 g of a mixture containing 70% by weight of water and 30% by weight of glycerol and subsequently dried. The weight of the catalytically active composition applied in this way, determined on a sample of the precatalyst obtained, was, after heat treatment at 400° C. for ½ hour, 14.9% by weight, based on the total weight of finished catalyst.

c) Preparation of Phthalic Anhydride Using the Comparative Catalyst 6a and Using the Catalyst 6b According to the Present Invention 135 g of the catalyst 6a or 135 g of the catalyst 6b were introduced into an iron tube having a length of 80 cm and an internal diameter of 15 mm. To regulate the temperature, the iron tube was surrounded by a salt melt. 360 standard l/h of air having loadings of 98.5% purity by weight o-xylene of 40–50 g of o-xylene/standard $m^3$ of air were passed through the tube from the top downward. After the reaction was complete, the samples of catalyst taken from the reactor were examined to determine their phase composition and BET surface area. These studies were carried out on a sample abraded from the shell of the catalyst removed from the reactor after the reaction was complete. The BET surface area was determined in accordance with DIN 66 131 and the phase composition was determined by X-ray structure analysis. FIG. 2 shows the X-ray powder diffraction pattern of this sample of material taken from the reactor. Comparison of the x-ray diffraction patterns in FIG. 1 and FIG. 2 provides evidence of the conversion of the multimetal oxides of the present invention into a mixture of silver-vanadium oxide bronzes under the conditions of PA production. Comparison of the X-ray diffraction patterns of FIG. 1 and FIG. 2 also shows that the multimetal oxides of the present invention are a new phase, i.e. a new compound, and do not consist of a mixture of silver-vanadium oxide bronzes. The results obtained are summarized in Table 5 below.

TABLE 5

| Catalyst | Salt bath temperature (° C.) | Conversion (%) | $CO_x$[1] Selectivity (%) | $C_8$[2] Selectivity (%) | Gross composition | Phase composition after reaction | BET surface area after reaction ($m^2/g$) |
|---|---|---|---|---|---|---|---|
| Comparative catalyst 6a | 400 | 30 | 20.1 | 78.4 | $Ag_{0.73}V_2O_x$ | $Ag_{0.73}V_2O_5$ (main component) | 0.4 |
|  | 420 | 44 | 23.4 | 74.0 |  |  |  |
|  | 440 | 55 | 25.8 | 72.1 |  | β-$Ag_{0.35}V_2O_5$ (secondary component) |  |
| 6b according to the present invention | 325 | 30 | 6.5 | 92.3 | $Ag_{0.73}V_2O_x$ | $Ag_{0.73}V_2O_5$ (main component) | 6.8 |
|  | 330 | 45 | 8.5 | 90.2 |  |  |  |
|  | 335 | 55 | 9.9 | 88.6 |  | β-$Ag_{0.35}V_2O_5$ (secondary component) |  |

The remaining selectivity to 100% relates to further by-products such as maleic anhydride, citraconic anhydride and benzoic acid
[1]$CO_x$ selectivity corresponds to proportion of combustion products (CO, $CO_2$)
[2]$C_8$ selectivity corresponds to proportion of phthalic anhydride and the intermediates o-tolualdehyde, o-toluic acid and phthalide.

EXAMPLE 7

Preparation of Benzoic Acid/Benzaldehyde Using the Comparative Catalyst 6a and Using the Catalyst 6b According to the Present Invention 135 g of the catalyst 6a or 6b were introduced into an iron tube having a length of 80 cm and an internal diameter of 15 mm. To regulate the temperature, the iron tube was surrounded by a salt melt. A gas mixture comprising 360 standard l/h of air and 30–40 standard l/h of steam having loadings of 99.5% purity by weight toluene of 40–50 g of toluene/standard $m^3$ of air was passed through the tube from the top downward. After the reaction was complete, the samples of catalyst taken from the reactor were examined to determine their phase composition and BET surface area, as described in Example 6c). The results obtained are summarized in Table 6.

TABLE 6

| Catalyst | Salt bath temperature (°C.) | Conversion (%) | $CO_x$[1] Selectivity (%) | $C_7$[2] Selectivity (%) | Gross composition | Phase composition after reaction | BET surface area after reaction ($m^2$/q [sic]) |
|---|---|---|---|---|---|---|---|
| Comparative catalyst 6a | 400 | 30 | 33.3 | 61.6[3] | $Ag_{0.73}V_2O_x$ | $\delta$-$Ag_{0.73}V_2O_5$ (main component) | 0.5 |
| | 420 | 44 | 38.2 | 55.1[4] | | $\beta$-$Ag_{0.35}V_2O_5$ (secondary component) | |
| 6b according to the present invention | 340 | 31 | 19.0 | 75.2[5] | $Ag_{0.73}V_2O_x$ | $\delta$-$Ag_{0.73}V_2O_5$ (main component) | 6.1 |
| | 350 | 45 | 23.2 | 71.4[6] | | $\beta$-$Ag_{0.35}V_2O_5$ (secondary component) | |

[1]$CO_x$ selectivity corresponds to the proportion of combustion products (CO, $CO_2$)
[2]$C_7$ selectivity corresponds to the proportion of the valuable products benzaldehyde and benzoic acid
[3]Benzaldehyde: 25.8%; Benzoic acid: 35.8%
[4]Benzaldehyde: 21.7%; Benzoic acid: 33.2%
[5]Benzaldehyde: 32.1%; Benzoic acid: 43.1%
[6]Benzaldehyde: 28.4%; Benzoic acid: 43.0%
The remaining selectivity to 100% relates to further by-products such as benzene, maleic anhydride and citraconic anhydride

We claim:

1. A multimetal oxide of the formula I $$Ag_{a-b}M_bV_2O*c\ H_2O,\quad I$$

where M is a metal selected from the group consisting of Li, Na, K, Rb, Cs, Tl, Mg, Ca, Sr, Ba, Cu, Zn, Cd, Pb, Cr, Au, Al, Fe, Co, Ni and/or Mo, a is from 0.3 to 1.9 and b is from 0 to 0.5, with the proviso that the difference (a−b) is greater than or equal to 0.1 and c is from 0 to 20 and x is a number determined by the valence and amount of elements different from oxygen in the formula I, which has a crystal structure giving an X-ray powder diffraction pattern which displays reflections at the lattice spacings d of 15.23±0.6, 12.16±0.4, 10.68+0.3, 3.41±0.04, 3.09±0.04, 3.02±0.04, 2.36±0.04 and 1.80+0.04 Å.

2. A multimetal oxide as claimed in claim 1 which has a fibrous crystal morphology having a mean ratio of fiber diameter to fiber length of less than 0.6.

3. A multimetal oxide as claimed in claim 1 which has a specific surface area determined by the BET method of from 3 to 250 $m^2$/g.

4. A multimetal oxide as claimed in claim 1 in which a is from 0.5 to 1.0, b is from 0 to 0.3 and c is from 0 to 5.

5. A multimetal oxide as claimed in claim 1 in which a is from 0.6 to 0.9, b is from 0 to 0.1 and c is from 0 to 1.

6. A multimetal oxide as claimed in claim 1 and having the formula $$Ag_aV_2O_x*c\ H_2O,$$

where a is from 0.6 to 0.9, x is as defined in claim 1 and c is from 0 to 5.

7. A multimetal oxide as claimed in claim 1 whose X-ray powder diffraction pattern displays the following 17 reflections at the specified lattice spacings d [Å]:

| Reflections | d [Å] |
|---|---|
| 1 | 15.23 ± 0.6 |
| 2 | 12.16 ± 0.4 |
| 3 | 10.68 ± 0.3 |
| 4 | 5.06 ± 0.06 |
| 5 | 4.37 ± 0.04 |
| 6 | 3.86 ± 0.04 |
| 7 | 3.41 ± 0.04 |
| 8 | 3.09 ± 0.04 |
| 9 | 3.02 ± 0.04 |
| 10 | 2.58 ± 0.04 |
| 11 | 2.48 ± 0.04 |
| 12 | 2.42 ± 0.04 |
| 13 | 2.36 ± 0.04 |
| 14 | 2.04 ± 0.04 |
| 15 | 1.93 ± 0.04 |
| 16 | 1.80 ± 0.04 |
| 17 | 1.55 ± 0.04. |

8. A multimetal oxide as claimed in claim 7 whose reflections 1 to 17 have the following approximate relative intensities ($I_{rel}$):

| Reflections | $I_{rel}$ [%] |
|---|---|
| 1 | 16 |
| 2 | 11 |
| 3 | 18 |
| 4 | 11 |
| 5 | 23 |
| 6 | 16 |
| 7 | 80 |
| 8 | 61 |
| 9 | 100 |
| 10 | 23 |
| 11 | 24 |
| 12 | 23 |
| 13 | 38 |
| 14 | 26 |
| 15 | 31 |
| 16 | 43 |
| 17 | 36. |

\* \* \* \* \*

UNITED STATES PATENT AND TRADEMARK OFFICE
CERTIFICATE OF CORRECTION

PATENT NO. : 6,849,574 B1
APPLICATION NO. : 09/830996
DATED : February 1, 2005
INVENTOR(S) : Heideman et al.

It is certified that error appears in the above-identified patent and that said Letters Patent is hereby corrected as shown below:

In Col. 4, line 26, the recitation of "Na, K, Cs, Ti, Mg, Ca, Sr, Ba, Cu, Zn, Cd, Pb, Cr, Au," should be replaced with --Na, K, Cs, Tl, Mg, Ca, Sr, Ba, Cu, Zn, Cd, Pb, Cr, Au,--

In Col. 6, line 62, the recitation of "As metals M, the metals Li, Na, X, Rb, Cs, Tl, Mg, Ca," should be replaced with --As metals M, the metals Li, Na, K, Rb, Cs, Tl, Mg, Ca,--

Signed and Sealed this

Twenty-seventh Day of November, 2007

JON W. DUDAS
*Director of the United States Patent and Trademark Office*